United States Patent
Crain et al.

(10) Patent No.: US 6,395,705 B2
(45) Date of Patent: *May 28, 2002

(54) METHOD AND COMPOSITION FOR TREATING IRRITABLE BOWEL SYNDROME USING LOW DOSES OF OPIOID RECEPTOR ANTAGONISTS

(75) Inventors: Stanley M. Crain, Leonia, NJ (US); Ke-fei Shen, Flushing; Gerald M. Fleischner, Chappaqua, both of NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/754,840

(22) Filed: Jan. 4, 2001

Related U.S. Application Data

(63) Continuation of application No. 09/261,361, filed on Mar. 3, 1999, now Pat. No. 6,194,382.

(51) Int. Cl.⁷ ........................ A61K 38/00; A61K 31/495
(52) U.S. Cl. ........................................... 514/2; 514/282
(58) Field of Search ....................................... 514/2, 282

(56) References Cited

U.S. PATENT DOCUMENTS 5,512,578 A * 4/1996 Crain et al. ................. 514/282
6,194,382 B1 * 2/2001 Crain et al. .................... 514/2

* cited by examiner

*Primary Examiner*—Raymond Henley, III
(74) *Attorney, Agent, or Firm*—Amster, Rothstein & Ebenstein

(57) ABSTRACT

This invention relates to a method for treating a subject with irritable bowel syndrome ("IBS") which comprises long-term administration of an opioid receptor antagonist at an appropriately low dose which will selectively antagonize excitatory opioid receptor functions, but not inhibitory opioid receptor functions, in myenteric neurons in the intestinal tract as well as in neurons of the central nervous system ("CNS"). The administration of the opioid receptor antagonist at a low dose enhances the potency of the inhibitory effects of endogenous opioid peptides present in the intestinal tract and the CNS, thereby reducing abdominal pain and stool frequency resulting from abnormally supersensitized excitatory opioid receptor functions. The invention also relates to a composition for treating a subject with IBS, which comprises an effective dose of an opioid receptor antagonist, and a pharmaceutically acceptable carrier.

12 Claims, No Drawings

METHOD AND COMPOSITION FOR TREATING IRRITABLE BOWEL SYNDROME USING LOW DOSES OF OPIOID RECEPTOR ANTAGONISTS

This is a continuation of application Ser. No. 09/261,361, filed Mar. 3, 1999, now U.S. Pat. No. 6,194,382, the contents of which are hereby incorporated by reference in their entirety.

FIELD OF THE INVENTION

This invention relates to a method for treating a subject with irritable bowel syndrome ("IBS") which comprises administering a low dose of an opioid receptor antagonist to the subject. Specifically, this invention relates to a method for treating a subject with IBS by the long-term administration of an opioid receptor antagonist at an appropriately low dose which will selectively antagonize excitatory opioid receptor functions, but not inhibitory opioid receptor functions, in myenteric neurons in the intestinal tract as well as in neurons of the central nervous system ("CNS"). The administration of the opioid receptor antagonist at a low dose enhances the potency of the inhibitory effects of endogenous opioid peptides present in the intestinal tract and the CNS, thereby reducing abdominal pain and stool frequency resulting from abnormally supersensitized excitatory opioid receptor functions. The invention also relates to a composition for treating a subject with IBS, which comprises an effective dose of an opioid receptor antagonist, and a pharmaceutically acceptable carrier.

BACKGROUND OF THE INVENTION

Irritable bowel syndrome is a functional bowel disorder in which abdominal pain is associated with defecation or a change in bowel habit. IBS has elements of an intestinal motility disorder, a visceral sensation disorder, and a central nervous disorder. While the symptoms of IBS have a physiological basis, no physiological mechanism unique to IBS has been identified. Rather, the same mechanisms that cause occasional abdominal discomfort in healthy individuals operate to produce the symptoms of IBS. The symptoms of IBS are therefore a product of quantitative differences in the motor reactivity of the intestinal tract, and increased sensitivity to stimuli or spontaneous contractions.

Due to a lack of readily identifiable structural or biochemical abnormalities in this syndrome, the medical community has developed a consensus definition and criteria, known as the Rome criteria, to aid in diagnosis of IBS. According to the Rome criteria, IBS is indicated by abdominal pain or discomfort which is (1) relieved by defection and/or (2) associated with a change in frequency or consistency of stools, plus two or more of the following: altered stool frequency, altered stool form, altered stool passage, passage of mucus, and bloating or feeling of abdominal distention (Dalton, C. and Drossman, D. A., *Am Fam Physician* 1997 55(3):875–880). Thus, a hallmark of IBS is abdominal pain that is relieved by defecation, and which is associated with a change in the consistency or frequency of stools. IBS may be diarrhea-predominant, constipation-predominant, or an alternating combination of both.

Persons with IBS exhibit hypersensitivity, particularly hyperalgesia, in response to painful distensions in the small bowel and colon and to normal intestinal function. Furthermore, there are also increased or unusual areas of visceral pain. The abdominal pain is often poorly localized, and may be migratory and/or variable in nature. The pain may be worsened by meals and reduced upon defecation. Furthermore, IBS symptoms, including hyperalgesia, are commonly initiated or exacerbated by stress (Dalton, C. and Drossman, D. A., *Am Fam Physician* 1997 55(3):875–880).

IBS is estimated to affect up to 20% of the adult population worldwide. Women apparently are more often affected than men, and the prevalence of irritable bowel syndrome is lower among the elderly (Camilleri, M. and Choi, M.-G., *Aliment Pharmacol Ther* 1997 11(1):3–15). It also seems clear that psychological factors, either stress or overt psychological disease, modulate and exacerbate the physiological mechanisms that operate in IBS (Drossman, D. A. et al., *Gastroenterology* 1988 95:701–708).

Some studies suggest that only about 10% to 50% of those afflicted with IBS actually seek medical attention. Nonetheless, IBS still accounts for up to about 3.5 million physician visits per year, and is the most common diagnosis in gastroenterologists' practice, accounting for about 25% of all patients (Camilleri and Choi, 1997). In a study published in 1993, persons afflicted with IBS were found to have more frequent doctor visits, a lower quality of life, and to miss three times as many days from work as those with no bowel symptoms (Drossman, D. A., *Dig Dis Sci* 1993 38:1569–1580). As a consequence, persons with IBS incur higher health care costs than those without IBS (Talley, N. J. et al., *Gastroenterology* 1995 109:1736–1741).

Attempts to treat IBS generally focus on either (1) treatments directed to the intestinal tract (so-called "end organ therapy") or (2) treatments directed to affective disorders mediated by the CNS which are associated with IBS (Farthing, M. J. G., *Drugs* 1998 56(1):11–21). Among the former are gut transit accelerants, such as wheat bran, soluble fiber, and polycarbophil calcium, for constipation-predominant IBS; antidiarrheals, such as loperamide, diphenoxylate, and codeine phosphate, for diarrhea-predominant IBS; and anticholinergics and smooth muscle relaxants, such as cimetropium bromide, pinaverium bromide, octilium bromide, trimebutine, and mebeverine, for diarrhea-predominant IBS and abdominal pain. In addition, alterations in diet have been targeted for those patients with food sensitivities or food allergies.

The end organ therapy treatments for IBS have proved ineffective or contain inherent drawbacks that limit their usefulness. For example, while the gut accelerants are useful to accelerate gut transit, they also exacerbate abdominal pain and bloating. Likewise, while antidiarrheals, such as loperamide, are often effective in treating diarrhea-predominant IBS, they are ineffective in treating the additional symptoms associated with IBS, such as abdominal pain. As a consequence, end organ therapy often is limited to patients with mild or moderate symptoms.

The anticholinergics and smooth muscle relaxants are effective in relieving pain associated with IBS, although their effects on other symptoms associated with IBS is unclear (Committee, *Gastroenterology* 1997 112:2120–2137; Pace, F. et al., *Digestion* 1995 56:433–442). In addition, some of the most effective compounds in these classes are not available for use in the United States, since they have not been approved by the Federal Food and Drug Administration (Committee, 1997). Finally, dietary alterations are of limited utility for a small segment of IBS patients.

Central nervous system treatments have received attention as potential IBS therapies because of the well recognized link between affective disorders and IBS, and also because of the disturbances in bowel health that occurs in individuals with these disorders. The tricyclic antidepressants, such as amitriptyline, imipramine, and doxepin, are frequently used to treat IBS, due to the neuromodulatory and analgesic properties of these compounds, which are independent of their psychotropic effects. However, because of their psychotropic properties, administration of these drugs requires long-term care, and are usually only given to patients with severe or refractory symptoms, impaired daily function, and associated depression or anxiety attacks. Furthermore, the newer antidepressants, in particular the specific serotonin reuptake inhibitors, such as fluoxetine, serraline, and paroxetine, have not been shown to be more effective than the tricyclic antidepressants, although some anecdotal evidence suggests these compounds may have fewer side effects (Committee, 1997).

Nalmefene glucuronide, an opioid receptor antagonist, has been investigated as a treatment for constipation-predominant IBS (Chami, T. N., et al., *Am J Gastroenterol* 1993 88:1568 [abstract]). Over an eight-week period, eight patients received 16 mg nalmefene glucuronide three times a week. While the patients reported decreased transit time and increased stool frequency, nalmefene glucuronide did not reduce abdominal pain or bloating, and stool consistency was not improved. The present inventors believe that the failure of nalmefene to treat pain associated with IBS can be attributed to the fact that this study used a high dose of nalmefene which antagonizes both excitatory and inhibitory opioid receptor-mediated functions in the gut as well as in the CNS. This view is supported by recent evidence that 1,000-fold lower doses of nalmefene (ca. 15 $\mu$g, IV) have been shown to markedly enhance morphine's analgesic potency (Joshi et al., *Anesthesiol.* 1999, in press), whereas doses of >0.5 mg markedly attenuate opioid analgesia (Konieczko, K. M. et al., *Br J Anaesth* 1988 61(3):318–23).

Recent reports of successful treatment of IBS patients with high doses of the kappa opioid agonist, fedotizine (30 mg, three times daily) (Dapoigny, M. et al., *Dig Dis Sci* 1995 40(10):2244–9; Gue, M. et al., *Gastroenterology* 1994 107 (5):1327–34) may be due to masking of supersensitized excitatory opioid receptor activity in the gut by activation of inhibitory opioid receptor functions, analogous to methadone maintenance of opioid addicts. Supersensitized excitatory opioid receptor functions in the gut may also result in tolerance to the analgesic effects of endogenous opioids (Wang, L. and Gintzler, A. R., *J Neurochem* 1995 64(3):1102–6), which could account for the abnormal visceral pain associated with IBS.

U.S. Pat. No. 5,512,578 discloses that the analgesic potency of bimodally-acting opioid agonists can be enhanced, and the tolerance/dependence liability reduced, upon coadministration of ultralow doses of selective excitatory opioid receptor antagonists. As used herein, "excitatory opioid receptor antagonists" are compounds that bind to and inactivate excitatory opioid receptors, but not inhibitory opioid receptors, on neurons in the nociceptive pathways. Such selective excitatory opioid receptor antagonists include, when administered at appropriately low doses, naloxone, naltrexone, etorphine, and dihydroetorphine. The selective excitatory opioid receptor antagonists attenuate excitatory, but not inhibitory, opioid receptor functions in nociceptive (pain) pathways of the peripheral and central nervous systems. As a result, symptoms associated with activation of excitatory opioid receptors, such as antianalgesia, hyperalgesia, hyperexcitability, physical dependence and/or tolerance effects, are blocked, whereas the analgesic effects of bimodally acting opioid agonists, which are mediated by the inhibitory opioid receptors, are unmasked and thereby enhanced (see Crain, S. M. and Shen, K.-F., *Proc Natl Acad Sci USA* 1995 92:10540–10544; Crain, S. M. and Shen, K.-F., *Trends Pharmacol Sci* 1998 19:358–365; *Ann NY Acad Sci* 1998 845:106–25; Shen, K.-F. and Crain, S. M., *Brain Res* 1997 757(2):176–90). The predictions based on these preclinical studies have been recently confirmed by clinical studies on postsurgical patients which demonstrated that cotreatment with morphine plus low-dose naloxone or nalmefene markedly enhanced the analgesic potency of morphine administered over 24-hour test periods (Joshi et al., *Anesthesiol.* 1999, in press; Gan, T. J. et al., *Anesthesiol.* 1997 87:1075–1081).

U.S. Pat. No. 5,512,578 further discloses that ultralow doses of naltrexone can, alone or in combination with low-dose methadone, provide effective longterm maintenance treatment for opioid addiction to prevent relapse to drug abuse. Furthermore, ultralow doses of selective excitatory opioid receptor antagonists can be administered alone to chronic pain patients to enhance the analgesic potency and reduce the tolerance/dependence liability of endogenous opioid peptides, such as enkephalins, dynorphins, and endorphins, which are elevated in chronic pain patients (Crain and Shen, 1995). However, there is no teaching or suggestion in U.S. Pat. No. 5,512,578 that administration of a selective excitatory opioid receptor antagonist would be useful in treating symptoms of IBS. In particular, there is no teaching or suggestion that administration of a selective excitatory opioid receptor antagonist would be useful in treating symptoms of IBS that are unrelated to the nociceptive pathways, such as stool frequency or consistency.

U.S. Pat. No. 5,472,943 also discloses a method wherein coadministration of an ultralow dose of a selective excitatory opioid receptor antagonist with a bimodally-acting opioid agonist selectively enhances the analgesic effect of the bimodally-acting opioid agonist while reducing the undesirable side-effects associated with longterm administration of the opioid agonist. However, U.S. Pat. No. 5,472,943 does not disclose that a selective excitatory opioid receptor antagonist can be used in the absence of a bimodally-acting opioid agonist.

Both U.S. Pat. Nos. 5,580,876 and 5,767,125 also disclose a method to selectively enhance the analgesic effect of a bimodally-acting opioid agonist while reducing unwanted side-effects associated with the administration of the opioid agonist by coadministration of the opioid agonist with an amount of an excitatory opioid receptor antagonist, such as naltrexone or nalmefene, effective to enhance the analgesic effect of the bimodally-acting opioid agonist while reducing the undesirable side-effects. U.S. Pat. Nos. 5,580,876 and 5,767,125 disclose use of an excitatory opioid receptor antagonist alone for treatment of opioid addicts, and do not teach or suggest that administration of a selective excitatory opioid receptor antagonist would be useful in treating symptoms of IBS. In particular, there is no teaching or suggestion that administration of a selective excitatory opioid receptor antagonist would be useful in treating other symptoms of IBS, such as stool frequency or consistency.

U.S. Pat. No. 5,585,348 relates to a method for reducing hyperalgesia associated with administration of nerve growth factor or related growth factors. The method comprises administration of a selective excitatory opioid receptor antagonist prior to or simultaneously with the administration of nerve growth factor. However, U.S. Pat. No. 5,585,348 does not disclose that the selective opioid receptor antagonist may be administered in the absence of nerve growth factor, and does not teach or suggest that the administration of a selective excitatory opioid receptor antagonist alone would be useful in treating IBS.

SUMMARY OF THE INVENTION

The present invention is directed to a method for treating a subject with IBS. The method comprises administering to the patient a low dose of an opioid receptor antagonist. In addition, the present invention provides a pharmaceutical composition, comprising an effective dose of an excitatory opioid receptor antagonist, and a pharmaceutically acceptable carrier.

DETAILED DESCRIPTION OF THE INVENTION

As used herein, "treating IBS" is considered to mean reducing or attenuating abdominal pain and reducing or attenuating one or more of abnormal consistency or abnormal frequency of stools associated with IBS in a patient. The present inventors have discovered that longterm administration of an excitatory opioid receptor antagonist can relieve symptoms associated with IBS, in particular the abdominal pain and the abnormal consistency and/or frequency of stools. Accordingly, the present invention is directed to a method for treating patients with IBS by longterm administration of appropriately low doses of an excitatory opioid receptor antagonist.

The primary concept of the present invention is that since remarkably similar bimodal excitatory and inhibitory opioid receptor functions have been demonstrated to exist in myenteric neurons in the intestine (Xu, H. et al., *Brain Res.* 1989 504(1):36–42; Gintzler, A. R., *Adv Exp Med Biol.* 1995 373:73–83; Wang and Gintzler, 1995) as occur in somatic sensory and CNS neurons (Shen, K.-F. and Crain, S. M., *Brain Res.* 1989 491(2):227–42; Crain, S. M. and Shen, K.-F., *Trends Pharmacol Sci.* 1990 11(2):77–81; Crain and Shen, 1998), selective antagonism of abnormal or supersensitized excitatory opioid receptor functions in gut neurons by low doses of an opioid receptor antagonist may enhance the analgesic effects of endogenous opioids on visceral sensory neurons and attenuate hypersensitivities and hyperexcitabilities of visceral sensory and visceral motor neurons involved in IBS.

Abnormal levels of endogenous opioid peptides may be generated in the gut by emotional stress, inflammatory or metabolic disorders, or intrinsic release from gut neurons. Excitatory opioid receptors in the gut may become supersensitized by chronic exposure to endogenous or exogenous bimodally-acting (excitatory/inhibitory) opioid agonists, as has been shown to occur in somatic sensory dorsal root ganglia ("DRG") neurons (Crain, S. M. and Shen, K.-F., *Brain Res.* 1992 575:13–24; Shen, K.-F. and Crain, S. M., *Brain Res* 1992 597:74–83). Neurons with supersensitized excitatory opioid receptor functions in the gut may therefore become "physically dependent" on opioids, just as occurs in somatic sensory and CNS neurons. Selective activation of excitatory opioid receptor functions by application of low (i.e., nM) concentrations of bimodally-acting opioid agonists to myenteric neurons in the guinea pig ileum enhances the high-K$^+$-stimulated release of the $\mu/\delta$ opioid peptide, Met-enkephalin, whereas high (i.e., $\mu$M) opioid concentrations inhibits Met-enkephalin release (Xu et al., 1989). Intermittent increases in the release of Met-enkephalin or other endogenous opioid peptides by activation of supersensitized excitatory opioid receptors in the gut could, therefore, exacerbate "dependence" and "withdrawal" symptoms associated with IBS via a positive-feedback cycle analogous to mechanisms proposed to mediate protracted opioid dependence in the CNS (Crain and Shen, *Brain Res* 1992, Crain and Shen, 1998). In addition, the release of the kappa opioid peptide, dynorphin, from the peripheral (as well as central) terminals of sensory neurons may also play a role in mediating hyperalgesic effects in IBS, in view of evidence obtained on DRG neurons in vitro and in vivo (Shen, K.-F. and Crain, S. M., *J Neurosci* 1994 14:5570–5579; Apfel, S. C. et al., *Neurosci* 1995 68:1199–1206).

Excitatory opioid receptor antagonists suitable for use in the present invention include, but are not limited to, nalmefene, naltrexone, naloxone, etorphine and dihydroetorphine, as well as similarly acting opioid alkaloids and opioid peptides (e.g., biphalin, see Horan, P. J. et al., *J Pharmacol Exp Ther.* 1993 265(3):1446–54; Shen, K.-F. and Crain, S. M., *Brain Res* 1995 701(1–2):158–66). Preferred excitatory opioid receptor antagonists are nalmefene and naltrexone, because of their increased duration of action as compared to naloxone and their greater bioavailability after oral administration.

Other excitatory opioid receptor antagonists suitable for use in the present invention may be identified by measuring their effect on the action potential duration ("APD") of DRG neurons in tissue cultures, as described in U.S. Pat. No. 5,472,943. In particular, excitatory opioid receptor antagonists of the present invention are compounds which selectively block prolongation of the APD of DRG neurons induced by low concentrations of morphine and other bimodally acting opioids (an excitatory opioid receptor effect), and unmask shortening of the APD (an inhibitory opioid receptor effect) in DRG neurons, which generally requires much higher concentrations of these bimodally-acting opioid receptor agonists (see U.S. Pat. No. 5,472,943).

The dose of an excitatory receptor antagonist to be administered would vary according to the specific pharmacologic properties of the opioid receptor antagonist employed and the characteristics of the IBS patient. For example, where the opioid receptor antagonist employed is naltrexone, in most cases the daily dose would be in a range between about 0.1 mg/day and about 5 mg/day. More preferably, the dose would be in a range between about 0.3 mg/day and about 3 mg/day. Where the opioid receptor antagonist employed is nalmefene, in most cases the daily dose would be in a range between about 0.01 mg/day and about 1 mg/day. The dose administered should be sufficient to relieve the abdominal pain and other symptoms associated with IBS, but not so high as to induce dysphoria or other adverse side effects caused by sustained blockage of inhibitory opioid receptor functions. At such a dose, the opioid receptor antagonist binds selectively to the excitatory opioid receptors on the myenteric and CNS neurons and thereby inactivates excessive excitatory opioid receptor-mediated functions, such as hyperexcitability, hyperalgesia, tolerance, physical dependence, and others. The inhibitory opioid receptor functions are not attenuated by these low doses of the opioid receptor antagonist. As a result, the excitatory opioid receptor antagonist treatment enhances the analgesic potency and decreases the undesirable side effects associated with chronic activation by endogenous bimodally-acting opioid peptides, including enkephalins, dynorphins and endorphins, which are markedly upregulated in chronic pain patients (Crain and Shen, 1995).

Naltrexone (50% mg tablets, DuPont Merck, tradenames Trexan or Revia) is currently approved by the FDA for longterm daily treatment of alcohol and opioid addiction. This treatment may also be effective in attenuating some types of IBS symptoms. However, at the relatively high dose employed in these treatments, naltrexone blocks all inhibitory as well as excitatory opioid receptor functions, thereby interfering with analgesia mediated by endogenous as well as exogenous opioids. Therefore, high-dose naltrexone or nalmefene (tradename Revex; Cheskin, L. J. et al., *Drug Alcohol Depend* 1995 39(2):151–4), by antagonizing inhibitory opioid receptors, will not reliably attenuate abdominal pain nor intestinal dysmotility underlying changes in the consistency or frequency of stools, and may also interfere with other important inhibitory opioid receptor-mediated functions in the central nervous system that regulate normal emotional and euphoric states. Accordingly, low dose, selective excitatory opioid receptor antagonist therapy offers an attractive alternative that reliably attenuates abdominal pain and intestinal dysmotility underlying changes in the consistency or frequency of stools, while retaining significant inhibitory opioid receptor-mediated functions in the peripheral and central nervous system.

The excitatory opioid receptor antagonists for use in the present invention may be in the form of free bases or pharmaceutically acceptable acid addition salts thereof. Examples of suitable acids for salt formation include but are not limited to methanesulfonic, sulfuric, hydrochloric, glucuronic, phosphoric, acetic, citric, lactic, ascorbic, maleic, and the like.

The excitatory opioid receptor antagonist may be administered to a human or animal subject by known procedures including but not limited to orally, sublingually, parenterally, transdermally, and by suppository.

The excitatory opioid receptor antagonists may be formulated in compositions with a pharmaceutically acceptable carrier. The carrier must be "acceptable" in the sense of being compatible with the other ingredients of the formulation and not deleterious to the recipient thereof. Examples of suitable pharmaceutical carriers include lactose, sucrose, starch, talc, magnesium stearate, crystalline cellulose, methyl cellulose, carboxymethyl cellulose, glycerin, sodium alginate, gum arabic, powders, saline, water, among others. The formulations may conveniently be presented in unit dosage and may be prepared by methods well-known in the pharmaceutical art, by bringing the active compound into association with a carrier or diluent, as a suspension or solution, and optionally one or more accessory ingredients, e.g. buffers, flavoring agents, surface active agents, and the like. The choice of carrier will depend upon the route of administration.

For oral and sublingual administration, the formulation may be presented as capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate.

For parenteral administration, the opioid receptor antagonist may combined with a sterile aqueous solution which is preferably isotonic with the blood of the recipient. Such formulations may be prepared by dissolving solid active ingredient in water containing physiologically compatible substances such as sodium chloride, glycine, and the like, and having a buffered pH compatible with physiological conditions to produce an aqueous solution, and rendering said solution sterile. The formulations may be present in unit or multi-dose containers such as sealed ampoules or vials.

For transdermal administration, the opioid receptor antagonist may be combined with skin penetration enhancers such as propylene glycol, polyethylene glycol, isopropanol, ethanol, oleic acid, N-methylpyrrolidone, and the like, which increase the permeability of the skin to the compounds, and permit the compounds to penetrate through the skin and into the bloodstream. The antagonist/enhancer compositions also may be combined additionally with a polymeric substance such as ethylcellulose, hydroxypropyl cellulose, ethylene/vinylacetate, polyvinyl pyrrolidone, and the like, to provide the composition in gel form, which can be dissolved in solvent such as methylene chloride, evaporated to the desired viscosity, and then applied to backing material to provide a patch.

For administration by suppository, the opioid receptor antagonist may be combined with any appropriate base to form a mass that is solid at room temperature but dissolves at body temperature. The base may include, without limitation, cocao butter, glycerinated gelatin, hydrogenated vegetable oils, polyethylene glycols of various molecular weights, fatty acid esters of polyethylene glycols, and the like.

The amount of the excitatory opioid receptor antagonist administered is an amount effective to attenuate abdominal pain and intestinal dysmotility which produces changes in the consistency or frequency of stools and thereby enhance the analgesic potency of endogenous opioid peptide agonists in the intestinal tract and in the CNS. That is, the opioid receptor antagonist is administered at a low dose which blocks the effects of bimodally-acting opioid peptide agonists on higher-affinity excitatory opioid receptors without blocking the effects on inhibitory opioid receptors. This amount is readily determinable by one skilled in the art (Crain and Shen, 1995, 1998; Shen and Crain, 1997).

The present invention is described in the following Clinical Study which is set forth to aid in the understanding of the invention, and should not be construed to limit in any way the invention as defined in the claims which follow thereafter.

CLINICAL STUDY

An open study of low dose naltrexone administration in four (4) patients with IBS was initiated. The patients were evaluated for IBS, based on the Rome criteria. All patients were screened for other disorders or medications that could cause gastrointestinal symptoms of IBS. These included inflammatory bowel disease, cancer, lactose intolerance, and neurological disorders, as well as the use of narcotic medications. Each patient was considered to be significantly incapacitated by their symptoms. Each subject was fully informed of the benefits and possible side effects of the study and thereafter freely gave their consent to participate in the study.

Each patient maintained a daily diary of the symptoms prior to and during treatment with 1–3 mg/day of naltrexone. Each participant noted the following symptoms:

1. Pain, relieved by defecation
2. Stool frequency
3. Stool consistency
4. Abdominal distension
5. Passage of mucus
6. Completion of evacuation In addition, each patient was asked to globally assess their subjective improvement on a scale of 0–4 (zero corresponding to no observable change, and 4 representing a marked and substantially improved state). Patients were permitted to remain on medications other than anticholinergics and antidiarrheal agents (i.e., fiber bulking agents or lactose enzyme replacement if needed).

Naltrexone (tradename Revia; 50% mg tablets; DuPont Merck) was purchased at a pharmacy. Single tablets were crushed and dissolved in 50% ml boiled distilled water, and stored unfrozen in a refrigerator. Each patient received 2 ml (2 mg) orally each morning with breakfast. Medication was prepared weekly and used for seven doses, with the remainder being discarded. None of the four patients reported discernible side effects.

Patient A was a 64-year-old male with lifelong symptoms of cramping abdominal pain and unformed bowel movements associated with mucus, usually in the morning, about 4–8 times per day. After nine months of treatment, Patient A reported that stool frequency was reduced to 1–2 formed bowel movements per day with no cramping abdominal pain. Patient A assessed his global improvement on the 0–4 scale as 4.

Patient B was a 71-year-old female with constipation episodes accompanied by cramping abdominal pain over a nine-year period. After a sigmoid resection for bleeding from a diverticulum two years ago, she had 10–12 diarrheal movements per day with increased cramping that was unresponsive to antidiarrheals (loperamide) and a calcium carbophil bulking agent (2 tablets with meals). After 75 days of treatment, Patient B reported stool frequency was reduced to 2–4 bowel movements per day with total elimination of abdominal pain associated with cramping. Patient B assessed her global improvement on the 0–4 scale as 3.

Patient C was a 63-year-old male reporting symptoms of abdominal cramping pain, particularly at night, abdominal distension, and 2–3 loose bowel movements daily. After 75 days of treatment with 2 mg/day of naltrexone, Patient C reported his abdominal pain associated with cramping had been eliminated, and his loose bowel movements had been halved in frequency. Patient C assessed his global improvement on the 0–4 scale as 2.5.

Patient D was a 42-year-old male who, over a three and a half year period of care, had reported 7–10 unformed diarrheal movements per day, with incapacitating abdominal cramping at various periods throughout the day. He was also known to be lactose intolerant, and was being ameliorated by a lactose free diet and enzyme replacement therapy at meals. Patent D required daily loperamide and anticholinergics prior to initiation of the study. Upon initiation of low dose naltrexone treatment, Patient D reported immediate relief of abdominal cramping symptoms and reduction in stool frequency by 50% percent. This improvement has continued over a 70 day treatment period, except when Patient D noted intake of alcoholic beverages (equivalent to ca. 25–35 gm equivalent of ethyl alcohol), whereupon IBS symptoms recurred for the next twenty-four hours. Patient D assessed his global improvement on the 0–4 scale as 2.5.

Patients A and C both attempted to change dosing schedules to every other day during the treatment period. In both cases, IBS symptoms returned, and remained until the daily treatment schedule was restored. Patient A also noted a return of symptoms when he traveled and forgot to pack his medication.

A followup of each patient was performed 24 months after the start of the study. After 24 months of treatment, Patient A was on a schedule of 2.5–3.0 mg naltrexone/day, corresponding to a dose of 25–30 μg/kg body weight/day. Patient A reported that his abdominal cramping had completely ceased, and his frequency of bowel actions had returned to normal levels.

Patient B reported after 12 months of treatment that she was on a schedule of 1.5–2.3 mg naltrexone/day, corresponding to a dose of 30–45 μg/kg body weight/day. Patient B experienced a 50% reduction in abdominal cramping, but no change in the frequency of bowel actions.

After 24 months of the study, Patient C had been diagnosed with fibromyalgia, and his IBS symptoms did not respond. Patient C had been on a regimen of 1–2 mg naltrexone/day, corresponding to a dose of 14–27 μg/kg body weight/day. Patient C refused to escalate the dose of naltrexone, and naltrexone was stopped after 6 months.

Patient D reported after nine months of treatment that he was on a schedule of 2.5–3.0 mg naltrexone/day, corresponding to a dose of 25–30 μg/kg body weight/day. After 9 months of treatment, Patient D reported a 75% decrease in cramping, and a 20% reduction in frequency of bowel actions. At this point low-dose naltrexone treatment was halted, and IBS symptoms returned.

All publications and patents mentioned hereinabove are hereby incorporated by reference in their entirety.

Although the invention herein has been described with reference to particular embodiments, it is to be understood that these embodiments are merely illustrative of various aspects of the invention. Thus, it is to be understood that numerous modifications may be made in the illustrative embodiments and other arrangements may be devised without departing from the spirit and scope of the invention.

What is claimed is:

1. A method for treating irritable bowel syndrome in a subject in need of such treatment, comprising orally administering to said subject an amount of an excitatory opioid receptor antagonist formulated in a pharmaceutically acceptable carrier effective to treat irritable bowel syndrome in said subject, wherein said irritable bowel syndrome is characterized by abdominal pain and at least one of abnormal consistency and abnormal frequency of stools in said subject and said amount of said antagonist is effective to attenuate abdominal pain and at least one of abnormal consistency and abnormal frequency of stools in said subject.

2. The method according to claim 1, wherein said amount of the excitatory opioid receptor antagonist is effective to block at least one of hypersensitivity and hyperexcitability of visceral sensory and visceral motor neurons associated with irritable bowel syndrome.

3. The method according to claim 1, wherein said excitatory opioid receptor antagonist is a member selected from the group consisting of naltrexone, nalmefene, diprenorphine, naloxone, etorphine, dihydroetorphine, biphalin, and similarly acting opioid alkaloids or peptides.

4. The method according to claim 1, wherein said excitatory opioid receptor antagonist is naltrexone.

5. The method according to claim 4, wherein said naltrexone is administered at a dose effective to relieve abdominal pain associated with IBS and wherein said dose is further ineffective to induce dysphoria.

6. The method according to claim 4, wherein said naltrexone is administered at a dose between about 0.1 mg/day and about 5 mg/day.

7. The method according to claim 4, wherein said naltrexone is administered at a dose between about 0.3 mg/day and about 3 mg/day.

8. The method according to claim 4, wherein said naltrexone is administered at a dose between about 2 μg/kg body weight/day and about 70 μg/kg body weight/day.

9. The method according to claim 4, wherein said naltrexone is administered at a dose between about 4 μg/kg body weight/day and about 45 μg/kg body weight/day.

10. The method according to claim 1, wherein said excitatory opioid receptor antagonist is nalmefene.

11. The method according to claim 10, wherein said nalmefene is administered at a dose effective to relieve abdominal pain associated with IBS and wherein said dose is further ineffective to induce dysphoria.

12. The method according to claim 10, wherein said nalmefene is administered at a dose between about 0.01 mg/day and about 1 mg/day.

* * * * *